(12) United States Patent  
Gogarnoiu

(10) Patent No.: US 7,758,344 B2
(45) Date of Patent: Jul. 20, 2010

(54) ASYMMETRICAL DENTAL IMPLANT AND METHOD OF INSERTION

(75) Inventor: Dumitru Gogarnoiu, Wynnewood, PA (US)

(73) Assignee: Form and Function Dental Services, P.C., Wynnewood, PA (US)

( * ) Notice: Subject to any disclaimer, the term of this patent is extended or adjusted under 35 U.S.C. 154(b) by 446 days.

(21) Appl. No.: 11/711,815

(22) Filed: Feb. 26, 2007

(65) Prior Publication Data

US 2007/0148622 A1    Jun. 28, 2007

Related U.S. Application Data

(63) Continuation-in-part of application No. 11/282,929, filed on Nov. 18, 2005, now Pat. No. 7,618,258.

(51) Int. Cl.
*A61C 3/06* (2006.01)

(52) U.S. Cl. .................................................... 433/166

(58) Field of Classification Search ............... 433/118, 433/119, 165, 166, 173, 141–150, 164, 152, 433/125, 117, 86; 606/80, 99, 166–172
See application file for complete search history.

(56) References Cited

U.S. PATENT DOCUMENTS

| 2,280,927 | A | * | 4/1942 | Phillips ...................... 433/165 |
| 4,722,688 | A | | 2/1988 | Lonca |
| 5,030,095 | A | | 7/1991 | Niznick |
| 5,174,755 | A | | 12/1992 | Fukuda |
| 5,382,251 | A | | 1/1995 | Hood et al. |
| 5,536,266 | A | | 7/1996 | Young et al. |
| 5,549,690 | A | | 8/1996 | Hollister et al. |
| 5,571,015 | A | | 11/1996 | Siegmund |
| 5,577,912 | A | | 11/1996 | Prins |
| 5,683,466 | A | | 11/1997 | Vitale |
| 5,839,898 | A | | 11/1998 | Fernandes |
| 5,863,200 | A | | 1/1999 | Hamada et al. |
| 5,997,299 | A | | 12/1999 | Unger |

(Continued)

FOREIGN PATENT DOCUMENTS

DE    25 22 941    11/1976

(Continued)

OTHER PUBLICATIONS

Pitt-Easy Implant System, 2006 Product Catalog, Innova Sybron Dental Specialties, Mar. 2006, pp. 1-33.

(Continued)

*Primary Examiner*—Cris L Rodriguez
*Assistant Examiner*—Heidi M Eide
(74) *Attorney, Agent, or Firm*—RatnerPrestia

(57) ABSTRACT

An implant fixture is disclosed. The implant fixture includes an elongated body extending along a longitudinal axis. The elongated body includes a base portion having a non-circular cross section and a receiver adapted to receive a prosthetic. A root portion extends from the base portion away from the receiver. An extension portion extends from the root portion away from the base portion. The extension portion extends primarily along one side of the longitudinal axis. A kit containing a plurality of implant fixtures having different configurations is also disclosed. Further, a method of inserting the implant fixture into a patient is also disclosed. The method uses piezoelectrically generated energy to seat the implant fixture in the patient's bone.

13 Claims, 10 Drawing Sheets

U.S. PATENT DOCUMENTS

| | | | |
|---|---|---|---|
| 6,039,568 A | 3/2000 | Hinds | |
| 6,062,858 A * | 5/2000 | Hugo et al. | 433/119 |
| 6,164,969 A | 12/2000 | Dinkelacker | |
| 6,217,332 B1 | 4/2001 | Kumar | |
| 6,227,859 B1 | 5/2001 | Sutter | |
| 6,244,867 B1 | 6/2001 | Aravena et al. | |
| 6,273,721 B1 | 8/2001 | Valen | |
| 6,500,003 B2 | 12/2002 | Nichinonni | |
| D470,939 S | 2/2003 | Daftary | |
| 6,626,670 B1 * | 9/2003 | Lerner et al. | 433/122 |
| D490,901 S | 6/2004 | Schulter et al. | |
| 6,788,986 B1 | 9/2004 | Traber et al. | |
| 6,814,577 B2 | 11/2004 | Blacklock | |
| 6,843,653 B2 | 1/2005 | Carlton | |
| 6,854,972 B1 | 2/2005 | Elian | |
| 2003/0031982 A1 | 2/2003 | Abarno | |
| 2003/0064349 A1 | 4/2003 | Simmons, Jr. | |
| 2003/0143514 A1 | 7/2003 | Peltier | |
| 2004/0018470 A1 | 1/2004 | Fernendes et al. | |
| 2004/0029075 A1 | 2/2004 | Peltier et al. | |
| 2004/0185418 A1 | 9/2004 | Schulter et al. | |
| 2004/0185420 A1 | 9/2004 | Schulter | |
| 2005/0019730 A1 | 1/2005 | Gittleman | |
| 2005/0084821 A1 | 4/2005 | Sims et al. | |
| 2005/0119666 A1 | 6/2005 | Bubb | |
| 2005/0136378 A1 | 6/2005 | Ennajimi et al. | |
| 2005/0164146 A1 | 7/2005 | Cantor | |
| 2005/0266381 A1 | 12/2005 | Abarno | |

FOREIGN PATENT DOCUMENTS

| | | |
|---|---|---|
| DE | 295 09 919 U1 | 8/1995 |
| DE | 195 41 032 A1 | 5/1997 |
| EP | 0 962 192 A1 | 12/1999 |
| EP | 1 013 236 A1 | 6/2000 |
| WO | WO 01/34056 A1 | 5/2001 |
| WO | WO 01/50972 A2 | 7/2001 |
| WO | WO 03/047455 | 6/2003 |
| WO | WO 2005/079696 A1 | 9/2005 |

OTHER PUBLICATIONS

NobelSpeedy, Groovy Replace, Nobel Biocare Services AG, 2005, 8 pages.
Direct Abutment System, Astra Tech Implants, Aug. 2005, 6 pages.
Growing Your Business with Implants, Nobel Biocare Services AG, 2005, 16 pages.
The Zirconia Titanium Technology, Perio-Integration, T.B.R. Group, undated, 6 pages.
Piezosurgery, Mectron Medical Technology, www.mectron.com, printed Mar. 26, 2006, 5 pages.
Cellular Optic Airscaler & Tips, KaVo SONICflex LUX 2003L, undated, 6 pages.
The Revolutionary and New Dimension in Bone Surgery, Piezosurgery, undated, 2 pages.
Piezo Technologies—Piezo Ceramics and Ultrasonic Transducers, Advanced Piezoelectric Ceramics and Composites for Use in Ultrasonic Transducers and Arrays, Piezo Technologies, www.piezotechnologies.com/Engineering.htm, 2003-2006, pp. 1-3.
"Use of Site-Specific Anatomic Implants to Replace Missing Teeth," Fereidoun Daftary, Practical Procedures & Aesthetic Dentistry, Nov./Dec. 2005, vol. 17 No. 10, 4 pgs. Submitted for disclosure purposes only. Not admitted as prior art.
"A Concept for a Biologically Derived, Parabolic Implant Design," Robert L. Holt et al., The International Journal of Periodontics & Restorative Dentistry, 2002, vol. 22 No. 5, pp. 473-481.
"Nobel Perfect™ Esthetic Scalloped Implant: Rationale for a New Design," Peter S. Wöhrle, Clinical Implant Dentistry and Related Research, 2003, vol. 5 Supplement 1, pp. 64-73.
"Dentoalveolar Morphology: Evaluation of Natural Root Form Versus Cylindrical Implant Fixtures," Fereidoun Daftary, Practical Periodontics and Aesthetic Dentistry, May 1997, vol. 9 No. 4, pp. 469-478.
"Modeling and Characterization of the CEJ for Optimization of Esthetic Implant Design," German O. Gallucci et al., The International Journal of Periodontics & Restorative Dentistry, Feb. 2004, vol. 24 No. 1, pp. 19-29. un-numbered photo page.
www.nobelbiocare.com/global/en/DentalImplants/starting.htm, Nobel Biocare, Jul. 7, 2005. Submitted for disclosure purposes only. Not admitted as prior art.
www.cidemeeting.com/dental/dental_implants_nobel_biocare.htm, Jul. 7, 2005. Submitted for disclosure purposes only. Not admitted as prior art.
International Search Report with Written Opinion for international application No. PCT/US2006/027891, dated Jan. 19, 2007.
International Search Report for PCT International Application No. PCT/US2008/002129 mailed Sep. 19, 2008.

* cited by examiner

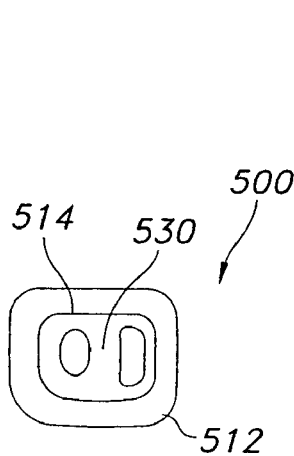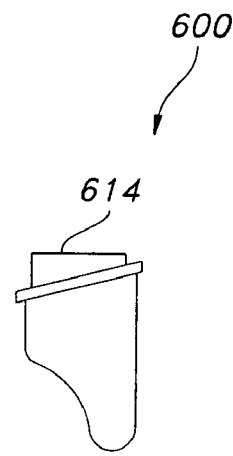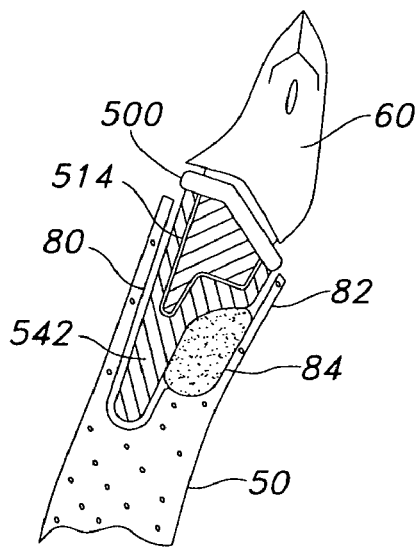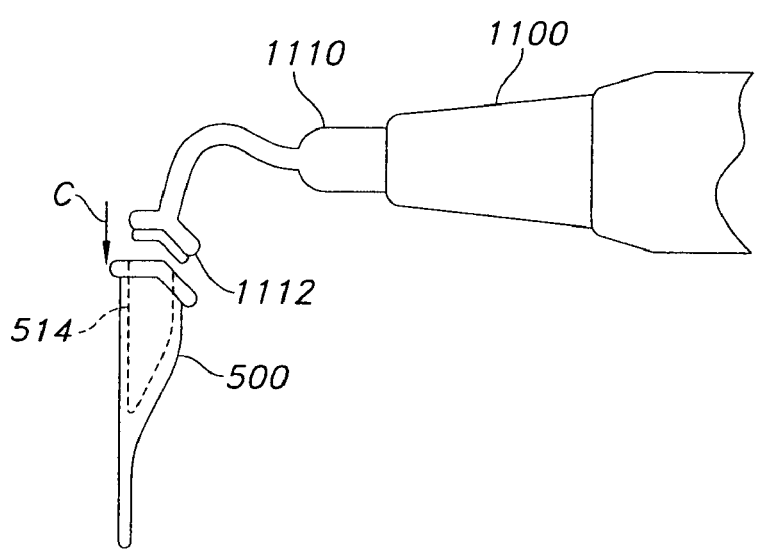

US 7,758,344 B2

ASYMMETRICAL DENTAL IMPLANT AND METHOD OF INSERTION

CROSS-REFERENCE TO RELATED APPLICATION

The present application is a Continuation-in-Part of U.S. patent application Ser. No. 11/282,929, filed on Nov. 18, 2005 now U.S. Pat. No. 7,618,258.

BACKGROUND OF THE INVENTION

Dental implants are used to anchor a mechanical fixture, such as a dental prosthesis, into living bone. The implant is embedded into the bone to provide a solid foundation for connecting the dental prosthesis. The implants and their respective dental prostheses serve numerous purposes, such as to assist the user with chewing, to provide a mating surface for an opposing tooth to prevent the loss of the opposing tooth, and to present an aesthetically pleasing appearance.

Prior to inserting the implant into the bone, the bone must be drilled to provide a recess for the insert to be implanted. Previously, implants were designed to be placed perpendicularly to the bone surface. The location of the implant in the user's mouth and the amount of mouth opening severely limit the ability to insert the head of the implant perpendicularly to the bone. Due to these limitations, most often, implants are inserted at an angle with respect to the bone surface. The angular insertion of an implant creates two problems: a) the mesial top portion of the implant is inserted too deeply into the bone, and, b) the distal top portion protrudes excessively from the bone. Furthermore, two problems arise at different stages of the treatment. The bone overgrows on the mesial aspect, thus requiring additional osseous surgery to remove excess bone. Later on, on the mesial aspect, the bone continues to resorb in order to accommodate biologic width. Biologic width is approximately 2 millimeters of connective tissue that wraps around a natural tooth or an implant and is constant. Violation of this area creates chronic inflammation and bone resorption.

To attempt to compensate for these problems, other prior art implants have been provided that disclose a top face that extends in a single plane oblique to a longitudinal axis of the implant. Such implants provide improved mechanical properties and anchorage but do not address biological fit, the implant exit and its relationship to the gum tissue. It would be beneficial to provide a dental implant having a top face with multiple slants. Slants on the mesiodistal aspect allow an angulated insertion of the top of the implant, having the top of the implant parallel to the bone surface and thus enabling a smooth development of biological width. The facial slant yields better aesthetic results due to the curved outline at the gum level.

A still further problem arises with implants after insertion into the mouth. Implants are threaded to secure the implant into the bone. The implants are axially symmetrical in order to enable such threading. Implants that are threaded and axially symmetrical do not anatomically fit the tooth roots, leaving a gap between the implant and bone in the coronal aspect, requiring significant time for healing. Such implants are prone to losing their primary stability, which is an important step in osseointegration. Osseointegration is the process by which the bone grows adjacent to the implant. Placement of an axially asymmetrical implant is less traumatic than the present rotational insertion method of an axially symmetric implant. It would be beneficial to provide an implant that is axially asymmetric and that fits the site of the extraction (body cavity) with little or no gap between implant and bone.

SUMMARY OF THE INVENTION

Briefly, the present invention provides an implant fixture. The implant fixture comprises an elongated body extending along a longitudinal axis. The elongated body includes a base portion having a non-circular cross section, a receiver adapted to receive a prosthetic. A root portion extends from the base portion away from the receiver. An extension portion extends from the root portion away from the base portion. The extension portion extends primarily along one side of the longitudinal axis.

Additionally, the present invention provides a kit comprising a plurality of implant fixtures described above. At least a first implant fixture of the kit has a different configuration from a second implant fixture of the kit.

Further, the present invention provides a method of inserting an implant fixture into a body cavity using a piezoelectric insertion tool. The method comprises attaching the implant fixture to the piezoelectric insertion tool; inserting the implant fixture into the body cavity; and seating the implant fixture in the body cavity based on energy from the piezoelectric insertion tool.

Also, the present invention provides a device for forming a cavity in a bone. The device comprises a first portion releasably couplable to a piezoelectric insertion tool, a second portion extending along a longitudinal axis, and a flange disposed between the first portion and the second portion. The flange extends along a plurality of planes. At least one of the plurality of planes extends obliquely relative to the longitudinal axis.

BRIEF DESCRIPTION OF THE DRAWINGS

The foregoing summary, as well as the following detailed description of desired embodiments of the invention, will be better understood when read in conjunction with the appended drawings, which are incorporated herein and constitute part of this specification. For the purposes of illustrating the invention, there are shown in the drawings embodiments that are presently desired. It should be understood, however, that the invention is not limited to the precise arrangements and instrumentalities shown. In the drawings, the same reference numerals are employed for designating the same elements throughout the several figures. In the drawings:

FIG. 23 is an occlusal view of the dental implant shown in FIG. 19;

FIG. 24 is a facial side elevational view of a dental implant according to a sixth embodiment of the present invention;

FIG. 25 is a side elevational view, partially in cross section, of the implant of FIGS. 19-23 implanted into bone;

FIG. 32 is a side elevational view of a piezoelectric insertion tool being coupled to the implant of FIGS. 19-23.

DETAILED DESCRIPTION OF THE INVENTION

Certain terminology is used herein for convenience only and is not to be taken as a limitation on the present invention. The terminology includes the words specifically mentioned, derivatives thereof and words of similar import. The term "facial" is defined to mean a direction closer to the lips and cheek of the user. The term "lingual" is defined to mean a direction closer to the tongue of the user. The term "mesial" is defined to mean a direction closer to an imaginary centerline of the mouth of the user. The term "distal" is defined to mean a direction farther from the imaginary centerline of the mouth. The term "occlusal" is defined to mean the top surface, such as the chewing surface, of a tooth. Further, as used herein, the term "configuration" is defined to mean size and/or shape. The following describes desired embodiments of the invention. However, it should be understood based on this disclosure, that the invention is not limited by the desired embodiments of the invention.

Referring generally to the figures, several embodiments of a dental implant according to the present invention are shown. Dental implants are used to provide an anchor in a mouth for a prosthetic tooth, also known as a crown.

Figure 1:
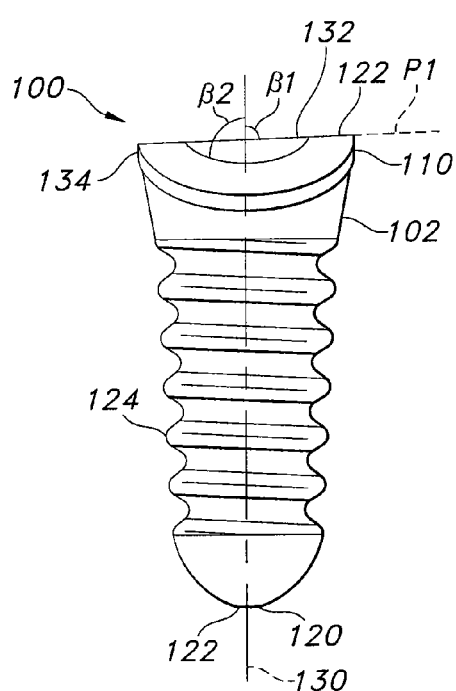
FIG. 1 is a facial side elevational view of a dental implant according to a first embodiment of the present invention.
Figure 2:
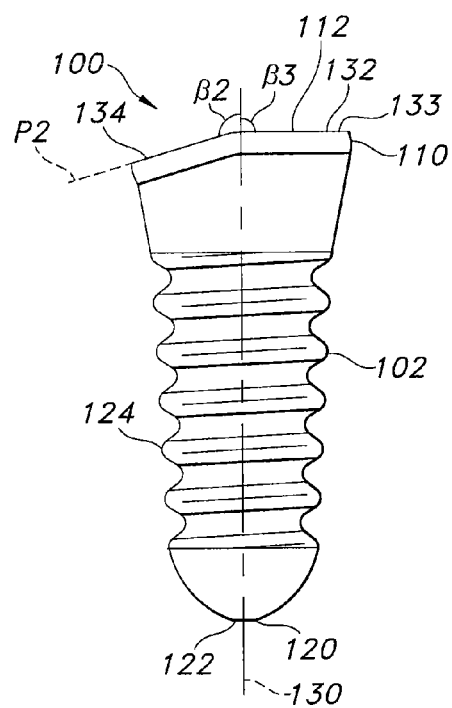
FIG. 2 is a mesial side elevational view of the dental implant shown in FIG. 1.
Figure 3:
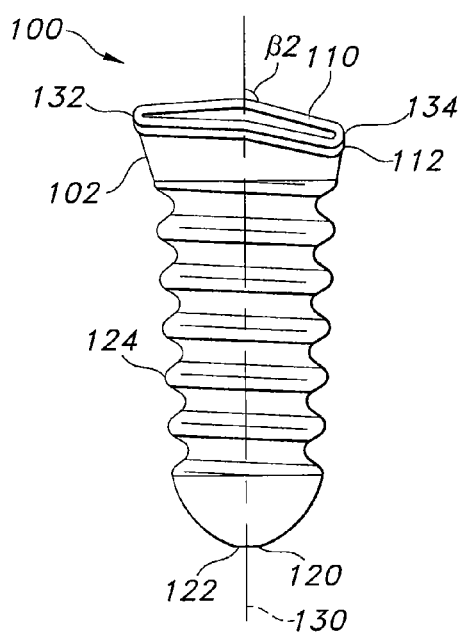
FIG. 3 is a distal side elevational view of the dental implant shown in FIG. 1.
Figure 4:
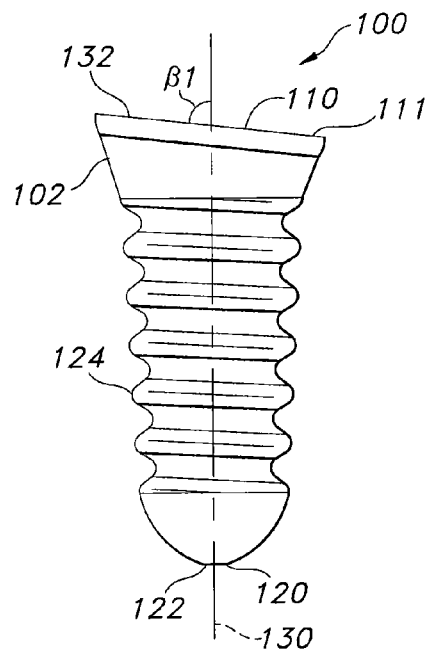
FIG. 4 is a lingual side elevational view of the dental implant shown in FIG. 1.
Figure 5:
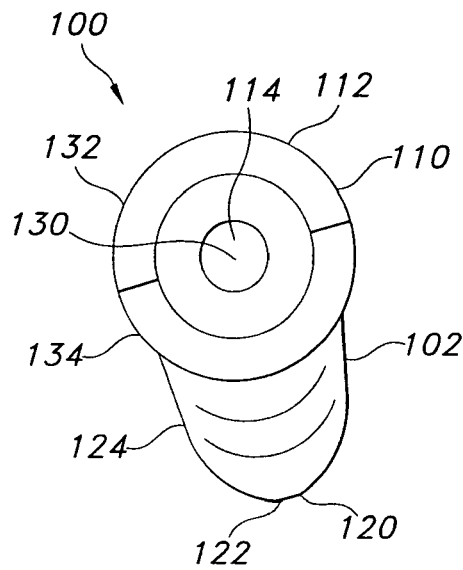
FIG. 5 is an occlusal view of the dental implant shown in FIG. 1.
Figure 6:
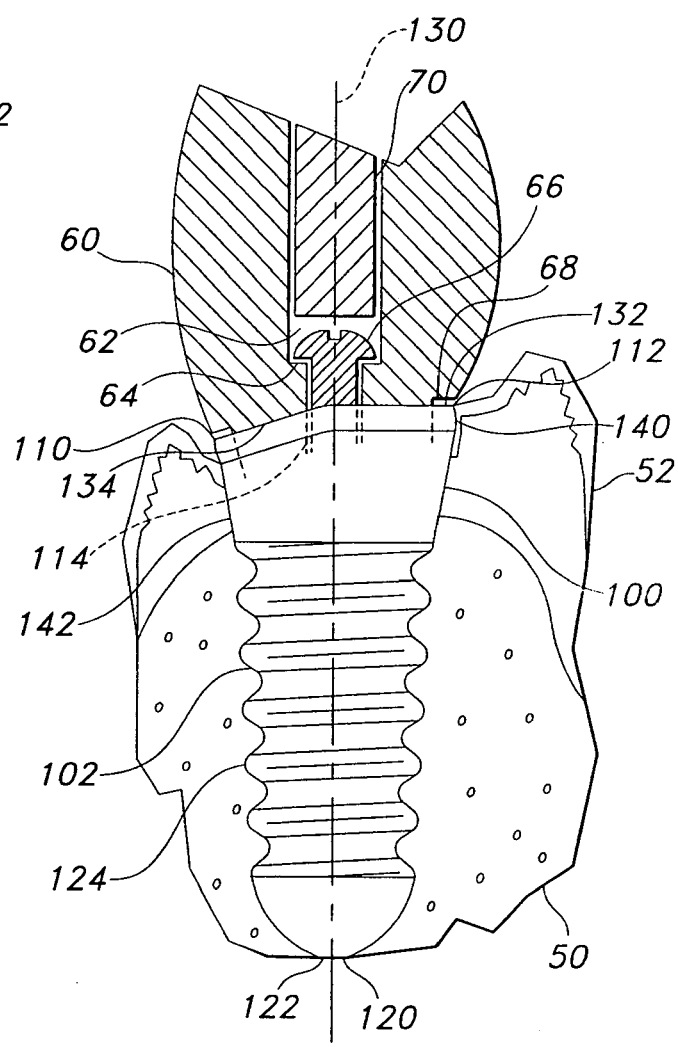
FIG. 6 is a mesial side view, partially in section, of the implant shown in FIG. 1 implanted into bone, with a dental prosthesis coupled to the implant.

FIGS. 1-5 show five different views of an implant 100 according to a first embodiment of the present invention. FIG. 1 is a facial view; FIG. 2 is a mesial view; FIG. 3 is a distal view; FIG. 4 is a lingual view; and FIG. 5 is an occlusal view of implant 100. FIG. 6 shows a partial sectional view of the mesial view of implant 100 having been inserted into a bone 50, with a prosthetic tooth or crown 60 connected to implant 100.

Referring to any of FIGS. 1-6, implant 100 includes a body 102 having a first end 110, a second end 120, and a longitudinal axis 130 extending between first end 110 and second end 120. First end 110 includes a top face 112. As seen in FIG. 5, desirably, top face 112 is generally annularly shaped with an opening 114 extending inward along longitudinal axis 130. Opening 114 provides a connection into which prosthetic tooth 60 is coupled.

Referring to FIGS. 1 and 4, top face 112 includes a first portion 132 that is slanted at a first angle β1 relative to longitudinal axis 130. Desirably, first portion 132 extends obliquely relative to longitudinal axis 130. First portion 132 forms a slanted mesiodistal face. Referring to FIGS. 1-3, top face 112 also includes a second portion 134 that is slanted at a second angle β2 relative to longitudinal axis 130. Second portion 134 forms a slanted facial face. Second portion 134 extends obliquely to longitudinal axis 130 and also at an angle to first portion 132. Second portion 134 may be slanted obliquely relative to first portion 132, or alternatively, second portion 134 may extend perpendicularly to first portion 132. Both slanted mesiodistal face and facial face may have angles β1, β2 that vary from shallow to steep, depending on the facial contours of the patient into which implant 100 is being inserted. Desirably, each angle β1, β2 extends between about 5 degrees and 45 degrees relative to longitudinal centerline 130, although those skilled in the art will recognize that angles β1, β2 may extend at different angles as well. Further, while first and second portions 132, 134 are depicted in FIGS. 2, 3, and 6 to extend approximately one half of top face 112, those skilled in the art will recognize that first and second portions 132, 134 may extend along different distances of top face 112.

With first and second portions 132, 134 slanting at different angles β1, β2, top face 112 can be said to have a compound slant relative to longitudinal axis 130. For implant 100 shown in FIGS. 1-5, the compound slant is a mesiodistal slant and a facial slant. Only a mesiodistal slant and a facial slant will satisfy the clinical requirements of both aesthetics and functionality for implant 100. These slants allow implant 100 to obtain perfect or near perfect alignment with the coronal part of the edentulous ridge of bone 50 after insertion.

Top face 112 also includes a third portion 133 that is slanted at a third angle β3 relative to longitudinal axis 130. Third portion 133 forms a lingual face. While third angle β3 is shown in FIG. 2 as extending approximately 90 degrees between lingual face and longitudinal axis 130, those skilled in the art will recognize that angle β3 may be more or less than 90 degrees.

Top face 112 is formed by a first plane P1 that extends along first portion 132 and out of the plane of FIG. 1 obliquely to longitudinal axis 130 along both a mesiodistal plane and also in a facial plane, and also a second plane P2 that extends along second portion 134 and out of the plane of FIG. 2 obliquely to longitudinal axis 130 along both the mesiodistal plane and also in a lingual plane. As can be seen from FIGS. 1 and 2, both planes P1, P2 extend obliquely relative to longitudinal axis 130. An intersection of planes P1 and P2 form a line that extends oblique to longitudinal axis 130.

Referring to FIG. 6, body 102 desirably includes a highly polished collar 140 that extends approximately 0.5 mm from first end 110 toward second end 120. Polished collar 140 allows the development of natural gingival sulcus around implant 100. A rougher surface 142 desirably extends approximately 1.5 mm below collar 140 toward second end 120. Rougher surface 142 accommodates biologic width of connective tissue 52 that typically surrounds a living tooth and provides a surface for connective tissue 52 to grow into after implant 100 is inserted into bone 50.

Referring to FIGS. 1-6, second end 120 is generally tapered from smaller to larger in a direction toward first end 110. Second end 120 is also closed with a rounded tip 122. Second end 120 also includes external threads 124 to form a threaded connection that may be used to secure implant 100 into bone 50, as shown in FIG. 6.

Referring now to FIG. 6 only, implant 100 is shown inserted into bone 50. Since implant 100 includes external threads 124, implant 100 may be screwed into bone 50 to provide a secure connection of implant 100 with bone 50.

After implant 300 is inserted into bone 50, crown 80 is secured to implant 300. Crown 80 includes a recess 82 extending longitudinally therethrough. A bottom part of recess 82 narrows, forming a lip 89. A coupling, such as a screw 86, is inserted through recess 82 and extends beyond crown 80 and into opening 314 for a threaded connection with mating threads (not shown) in opening 314. Screw 86 engages lip 89 to retain the head of screw 86 within recess 82. Bottom surface 84 of crown 80 is contoured to mate with top face 312 of implant 300 to provide a close fit between crown 80 and implant 300. After crown 80 is screwed onto implant 300, a filler 90 is inserted into recess 82 to cover screw 86.

Figure 7:
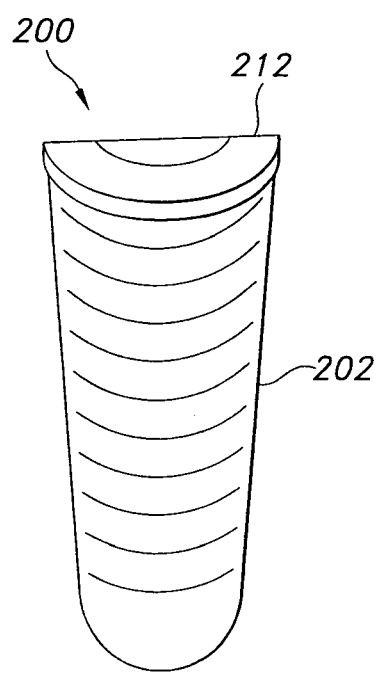
FIG. 7 is a facial side elevational view of a dental implant according to a second embodiment of the present invention.
Figure 8:
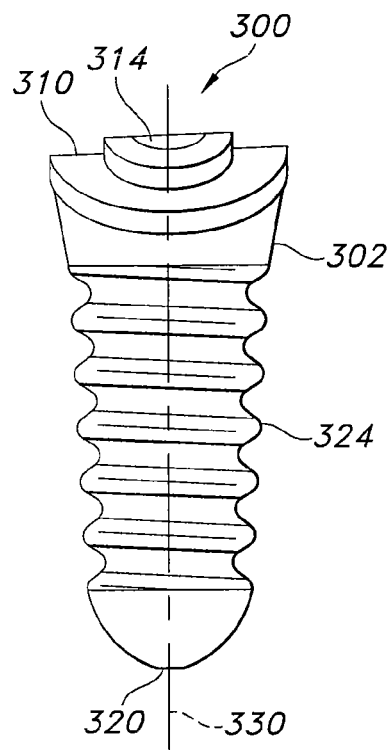
FIG. 8 is a facial side elevational view of a dental implant according to a third embodiment of the present invention.
Figure 9:
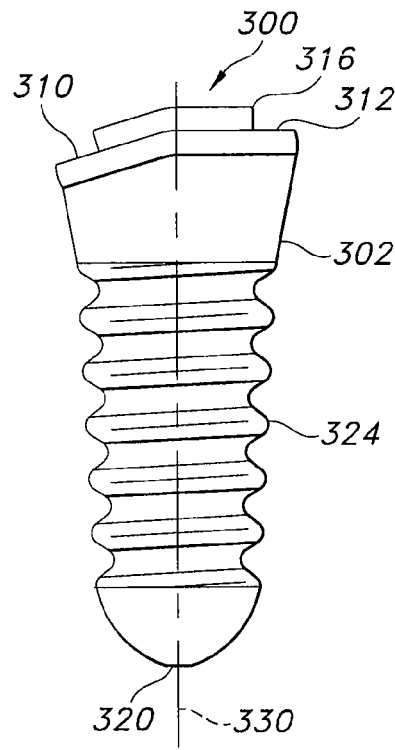
FIG. 9 is a mesial side elevational view of the dental implant shown in FIG. 8.
Figure 10:
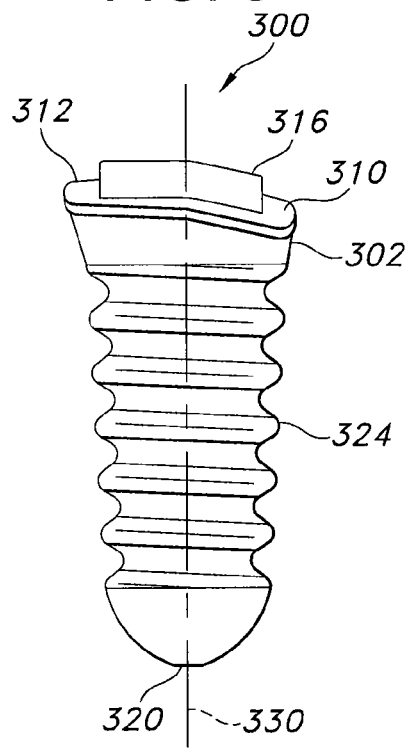
FIG. 10 is a distal side elevational view of the dental implant shown in FIG. 8.
Figure 11:
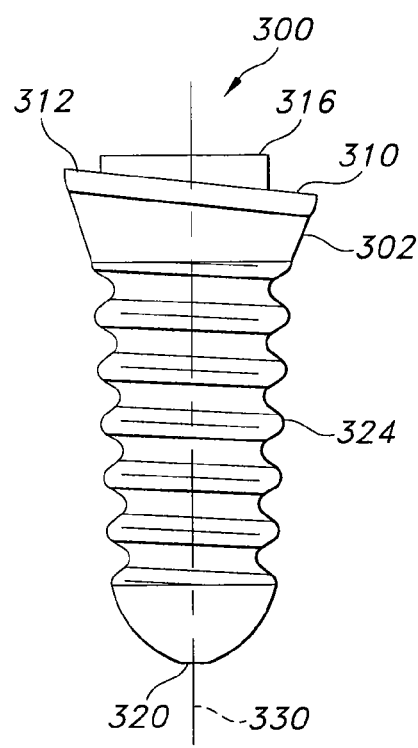
FIG. 11 is a lingual side elevational view of the dental implant shown in FIG. 8.

While external threads 124 provide a desired connection between implant 100 and bone 50, those skilled in the art will recognize that external threads 124 may be omitted, as seen in implant 200 shown in FIG. 7. Implant 200 includes a rough surface body 202. Body 202 may be press-fit into bone and may optionally be secured to bone with an adhesive (not shown). A top face 212 desirably has the same compound slant as top face 112 described above.

Figure 12:
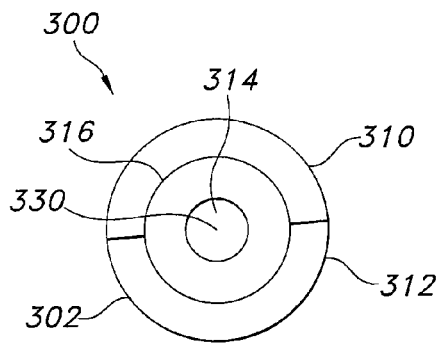
FIG. 12 is an occlusal view of the dental implant shown in FIG. 8.

Referring now to FIGS. 8-12, facial, mesial, distal, lingual, and occlusal views, respectively, of an alternate embodiment of an implant 300 are shown. Implant 300 includes a body 302 having a first end 310, a second end 320, and a longitudinal axis 330 extending between first end 310 and second end 320. First end 310 includes a top face 312. As seen in FIG. 12, desirably, top face 312 is generally annularly shaped with an opening 314 extending inward along longitudinal axis 330.

Figure 13:
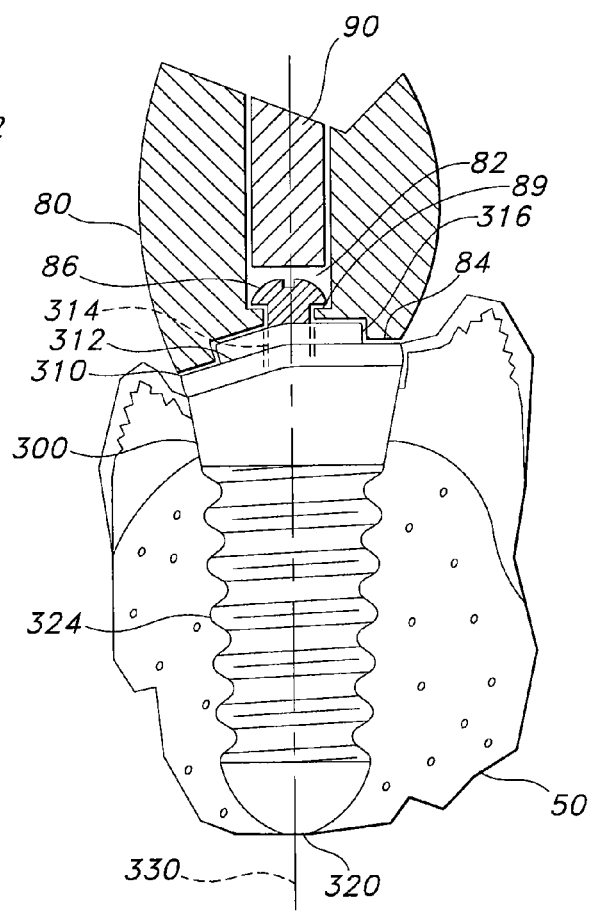
FIG. 13 is a mesial side view, partially in section, of the implant shown in FIG. 8 implanted into bone, with a dental prosthesis coupled to the implant.

An external connection 316 extends upward from top face 312, away from body 302. External connection 316 provides an alternate manner by which a crown 80, shown in FIG. 13, may be affixed to implant 300. Crown 80 includes a recess 82 that extends from the bottom of crown 80 upward. Recess 82 is sized to accept external connection 316 such that a bottom surface 84 of crown 80 rests on top face 312 of implant 300.

Bottom surface 84 of crown 80 is contoured to mate with top face 312 to provide a close fit between crown 80 and implant 300.

After implant 300 is inserted into bone 50, crown 80 is secured to implant 300. Crown 80 includes a passage 82 extending longitudinally therethrough. A bottom part of passage 82 narrows, forming a lip 89. A coupling, such as a screw 86, is inserted through passage 82 and extends beyond crown 80 and into opening 314 for a threaded connection with mating threads (not shown) in opening 314. Screw 86 engages lip 89 to retain the head of screw 86 within passage 82. Bottom surface 84 of crown 80 is contoured to mate with top face 312 of implant 300 to provide a close fit between crown 80 and implant 300. After crown 80 is screwed onto implant 300, a filler 90 is inserted into passage 82 to cover screw 86.

Figure 14:
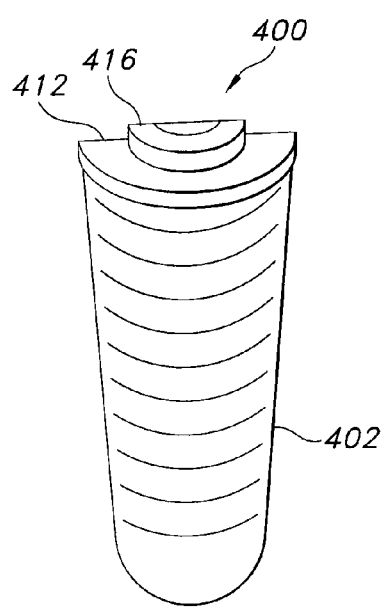
FIG. 14 is a facial side elevational view of a dental implant according to a fourth embodiment of the present invention.

Although implant 300 is shown in FIGS. 8-11 and 13 with threads 324, those skilled in the art will recognize that threads 324 may be omitted, such as in implant 400, shown in FIG. 14, which is similar to implant 200 shown in FIG. 7, having a rough surface body 402, but with an external connection 416 extending upward from a top face 412.

Desirably, implants 100, 200, 300, 400 are constructed from titanium, ceramic, or some other suitable biocompatible material. Those skilled in the art will also recognize that implants 100, 200, 300, 400 may be used to replace any tooth within a patient's mouth, and are not specific to any region in the mouth as long as the diameter of implants 100, 200, 300, 400 are varied and the angulations of top faces 112, 212, 312, 412 of each respective implant 100, 200, 300, 400 is varied according to the particular contours of the region.

Exemplary tools 1000 that may be used to form a body cavity 80 in bone 50 into which implants 100, 200, 300, 400 are to be inserted are shown in FIGS. 15-18. Tools 1000 may be supplied together in the form of a kit or, alternatively, tools 1000 may be provided separately.

Tools 1000 include a first tip 1010, a second tip 1030, a third tip 1050, and a fourth tip 1070. Although four tips 1010, 1030, 1050, and 1070 are disclosed, those skilled in the art will recognize that tools 1000 may include more or less than four tips.

Figure 15:
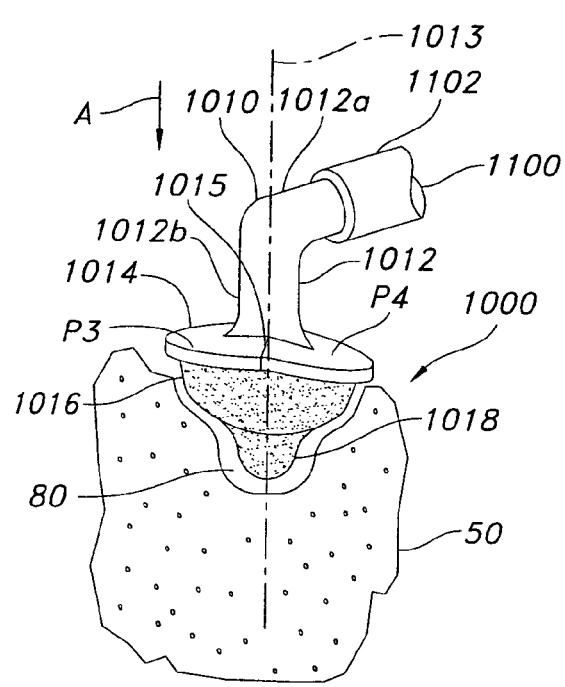
FIG. 15 is a distal view of a first insertion tip used to form a body cavity into which a dental implant shown in any one of FIGS. 1-14 may be inserted.

First tip 1010 includes a shaft 1012 that is releasably coupled to free end 1102 of piezoelectric tool 1100. Shaft 1012 bends approximately ninety degrees with a first end 1012a coupled to piezoelectric tool 1100 and a second end 1012b extending along a longitudinal axis 1013. Second end 1012b of shaft 1012 is connected to a generally circular flange 1014. Flange 1014 is formed along at least two planes, P3, P4 to mimic the compound angle of first end 110 of implant 100. At least one of planes P3, P4 extends obliquely relative to longitudinal axis 1013. FIG. 15 shows planes P3 and P4 intersecting at bend 1015.

As shown in each of FIGS. 15-18, the portion of bone 50 to the left side of tool 1000 is slightly higher than the portion of bone 50 to the right side of tool 1000. Bend 1015 in flange 1014 allows an operator to maintain an approximately even spacing between bone 50 and flange 1014 as first tip 1010 is inserted into bone 50 as body cavity 80 is formed.

Referring back to FIG. 15, a cutting face 1016 extends from flange 1014, along longitudinal axis 1013 and away from shaft 1012. Cutting face 1016 includes a generally concave exterior, with a rough cutting surface that extends around the entire perimeter of cutting face 1016. A nub 1018 extends from cutting face 1016, distally from flange 1014. Nub 1018 also includes a generally concave exterior with a rough cutting surface.

First tip 1010 is used to begin forming body cavity 80. When coupled to piezoelectric tool 1100 and applied to bone 50 in the direction shown by arrow A in FIG. 15, first tip 1010 vibrates at an ultrasonic frequency to drill into bone 50 and form body cavity 80. When flange 1014 approaches bone 50, first tip 1010 is removed from bone 50 and uncoupled from piezoelectric tool 1100.

Figure 16:
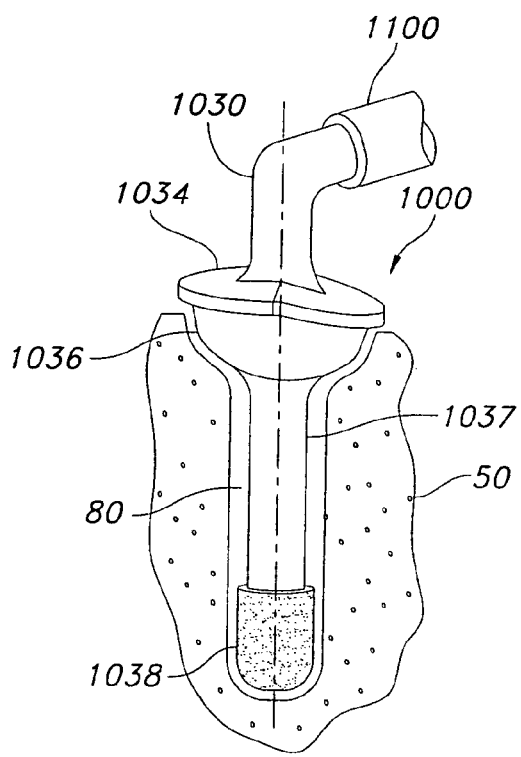
FIG. 16 is a distal view of a second insertion tip used to expand the body cavity shown in FIG. 15.

Referring now to FIG. 16, second tip 1030 is next coupled to piezoelectric tool 1100. Second tip 1030 is similar to first tip 1030 but instead of cutting face 1016 extending from flange 1014, second tip 1030 includes a generally concave exterior non-cutting face 1036 extending from a bent flange 1034. A generally cylindrical shaft 1037 extends from non-cutting face 1036. A generally cylindrical cutting nub 1038 having a rough cutting surface extends from shaft 1037. Cutting nub 1038 has a slightly larger diameter than nub 1018 so that body cavity 80 is enlarged diametrically upon application of second tip 1030 to body cavity 80.

Figure 17:
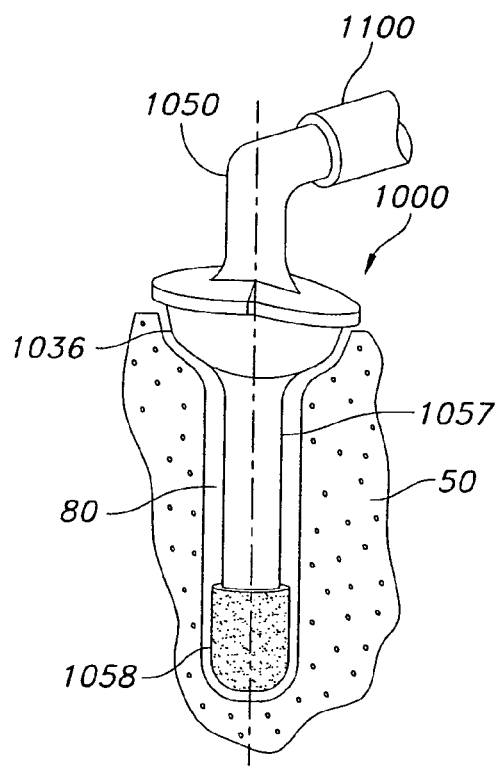
FIG. 17 is a distal view of a third insertion tip used to expand the body cavity shown in FIG. 16.
Figure 18:
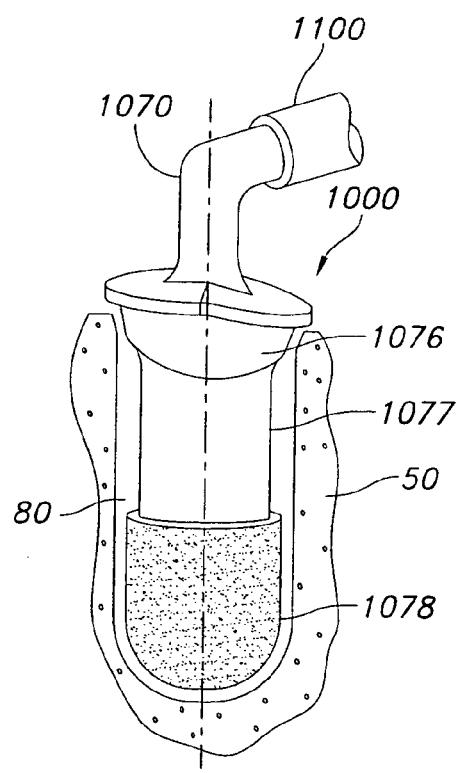
FIG. 18 is a distal view of a fourth insertion tip used to expand the body cavity shown in FIG. 17.

As shown in FIG. 17, third tip 1050 has a similar configuration as second tip 1030, but with a shaft 1057 that has a slightly larger diameter than shaft 1037 and a cutting nub 1058 having a rough cutting surface that has a slightly larger diameter than cutting nub 1038. Fourth tip 1070, shown in FIG. 18, has a similar configuration as third tip 1050, but with a shaft 1077 that has a slightly larger diameter than shaft 1057 and a cutting nub 1078 having a rough cutting surface that has a slightly larger diameter than cutting nub 1058. The diameter of cutting nub 1078 is at least the same size as that of non-cutting face 1076 such that body cavity 80 has a generally cylindrical shape as shown in FIG. 18. After body cavity 80 is formed, implant 100 is threaded into bone 50 surrounding body cavity 80 to the position shown in FIG. 6.

Figure 19:
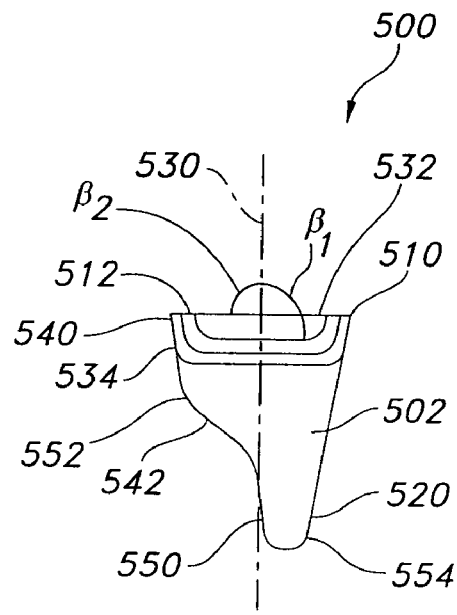
FIG. 19 is a facial side elevational view of a dental implant according to a fifth embodiment of the present invention.
Figure 20:
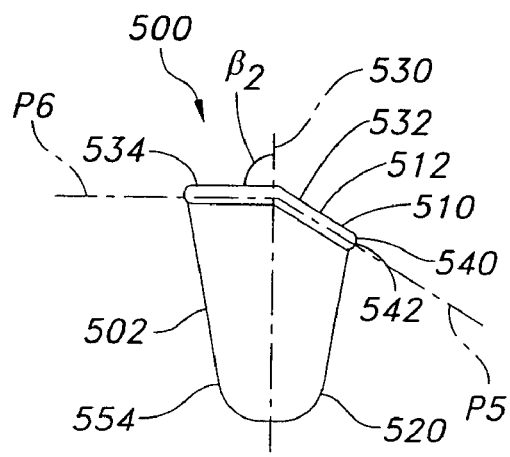
FIG. 20 is a mesial side elevational view of the dental implant shown in FIG. 19.
Figure 21:
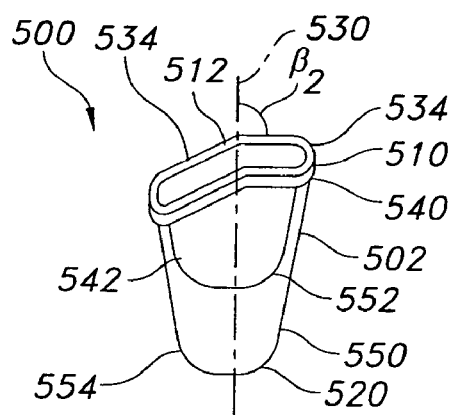
FIG. 21 is a distal side elevational view of the dental implant shown in FIG. 19.
Figure 22:
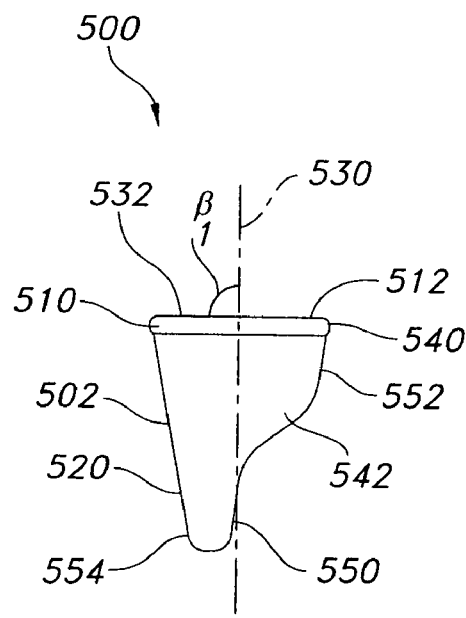
FIG. 22 is a lingual side elevational view of the dental implant shown in FIG. 19.

An alternate embodiment of a dental implant 500 according to the present invention is shown in FIGS. 19-23. FIG. 19 is a facial view; FIG. 20 is a mesial view; FIG. 21 is a distal view; FIG. 22 is a lingual view; and FIG. 23 is an occlusal view of implant 500. Desirably, implant 500 is constructed from titanium, zirconium, ceramic, or some other suitable biocompatible material.

Referring to any of FIGS. 19-22, implant 500 includes a body 502 having a first end 510, a second end 520, and a longitudinal axis 530 extending between first end 510 and second end 520. First end 510 includes a top face 512. As seen in FIG. 23, desirably, top face 512 is generally non-circular with an opening 514 extending inward along longitudinal axis 530. Opening 514 provides a connection into which crown 60 (shown in FIG. 25) is inserted. While opening 514 provides an internal connection with which to couple crown 60 to implant 500, those skilled in the art will recognize that an external connection 614 may extend upward from an alternate embodiment of an implant 600, shown in FIG. 24.

Referring back to FIG. 25, implant 500 is inserted into a body cavity 80 in a mouth, such as where a tooth (not shown) was previously removed. Body cavity 80 is defined by walls 82. An area of tender tissue 84 may be allowed to remain within bone 50 because implant 500 will be inserted into at least part of body cavity 80 that was formerly occupied by the tooth and its roots.

Referring back to FIGS. 19 and 22, top face 512 of implant 500 includes a first portion 532 that is slanted at a first angle β1 relative to longitudinal axis 530. Desirably, first portion 532 extends obliquely relative to longitudinal axis 530. First portion 532 forms a slanted mesiodistal face. Referring to FIGS. 20 and 21, top face 512 also includes a second portion 534 that is slanted at a second angle β32 relative to longitudinal axis 530. Second portion 534 forms a slanted facial face. Second portion 534 extends obliquely to longitudinal axis 530 and also at an angle relative to first portion 532. Second portion 534 may be slanted obliquely relative to first portion 532, or alternatively, second portion 534 may be perpendicular to first portion 532. Both slanted mesiodistal face and facial face may have angles β1, β2 that vary from shallow to steep, depending on the facial contours of the patient into which implant 500 is being inserted. Desirably, each angle β1, β32 extends between about 5 degrees and 45 degrees relative to longitudinal centerline 530, although those skilled in the art will recognize that angles β31, β32 may extend at different angles as well. Further, while first and second portions 532, 534 are depicted in FIGS. 20 and 21 to extend approximately one half of top face 512, those skilled in the art will recognize that first and second portions 532, 534 may extend along different distances of top face 512.

With first and second portions 532, 534 slanting at different angles β1, β32, top face 512 can be said to have a compound slant relative to longitudinal axis 530. For implant 500 shown in FIGS. 19-23, the compound slant is a mesiodistal slant and a facial slant. Only a mesiodistal slant and a facial slant will satisfy the clinical requirements of both aesthetics and functionality for implant 500. These slants allow implant 500 to obtain perfect or near perfect alignment with the coronal part of the edentulous ridge of bone 50 after insertion.

Top face 512 is formed along a first plane P5 that extends along first portion 532 and out of the plane of FIG. 20, and also a second plane P6 that extends along second portion 534 and out of the plane of FIG. 20. Both planes P5, P6 extend obliquely relative to longitudinal axis 530.

Referring to FIGS. 19-22, body 502 desirably includes a collar 540 that extends approximately 0.5 mm from first end 510 toward second end 520. A rougher surface 542 desirably extends below collar 540 toward second end 520. Referring to FIG. 21, rougher surface 542 provides a surface for bone 50 to grow into after implant 500 is inserted into bone 50.

Referring to FIGS. 19, 21, and 22, second end 520 forms a tapered root 550 that extends away from first end 510. As shown in FIGS. 19 and 22, second end 520, as well as root 550, extends asymmetrically about longitudinal axis 530. Root 550 includes a root portion 552 that extends from first end 510 and an extension portion 554 that extends from root portion 552, away from first end 510, and primarily along one side of longitudinal axis 530. While FIGS. 19 and 22 show a bottom end of extension portion 554 being totally along one side of longitudinal axis 530, those skilled in the art will recognize that a portion of bottom end of extension portion 554 may extend along the other side of longitudinal axis 530.

Root 550 has a generally convex face at an interface between root portion 552 and extension portion 544. Root 550 tapers from larger to smaller in a direction away from first end 510. The asymmetrical aspect of root 550 with respect to longitudinal axis 530 prevents rotation of implant 500 within body cavity 80 after insertion of implant 500 into body cavity 80. The convex face of root 550 generally mimics a tooth root and provides for a relatively comparable fit of root 550 within body cavity 80.

Referring back to FIG. 25, implant 500 is shown inserted into bone 50. Insertion of implant 500 into bone 50 will be described in detail later herein. After implant 500 is inserted into bone 50, crown 60 is secured to implant 500. Crown 60 may be secured to implant 500 in the same manner as described above with respect to implant 100, 300, shown in FIGS. 6 and 13.

Figure 26:
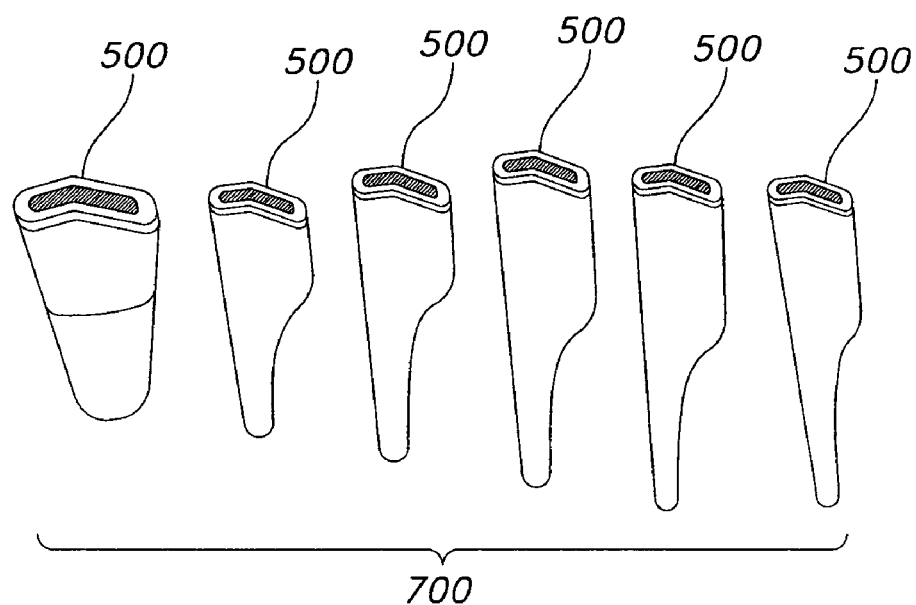
FIG. 26 is a side elevational view of a first embodiment of a kit of implants according to the present invention.

Implant 500 may be incorporated as part of a kit 700. As shown in FIG. 26, kit 700 may include a plurality of implants 500 that are intended for insertion into a predetermined implant location in a mouth, such as a lower bicuspid. Implants 500 in kit 700 are of different configurations, in that at least implants 500 in kit 700 differ in size from other implants in kit 700. With kit 700, an oral surgeon is able to select the best fit implant 500 from kit 700 based on the position in the mouth where implant 500 is to be inserted with a minimum amount of modification of the configuration of the selected implant 500.

Figure 27:
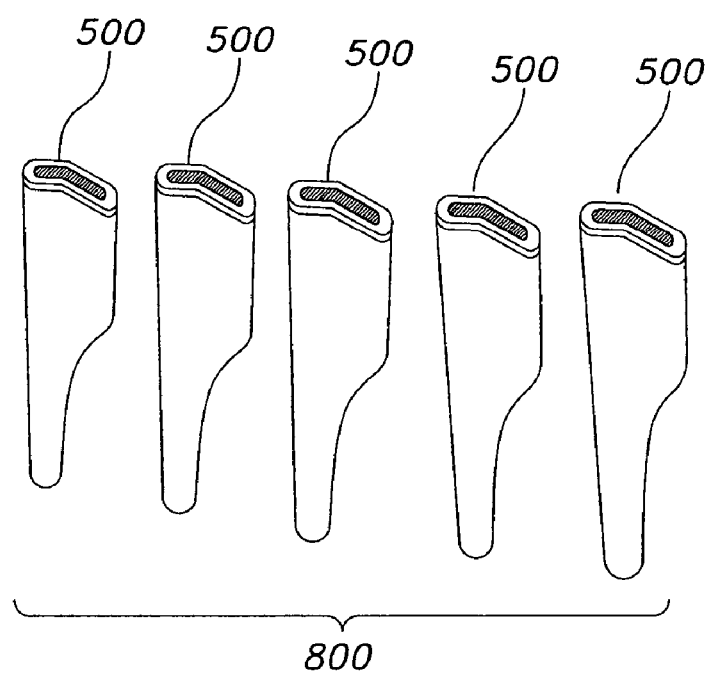
FIG. 27 is a side elevational view of a second embodiment of a kit of implants according to the present invention.

Alternatively, implant 500 may be incorporated as part of a kit 800. As show in FIG. 27, kit 800 may include a plurality of implants 500 that each correlate to a separate implant location within the mouth, such as a lower jaw, or one side of the lower jaw. Implants 500 are sized for a particular sized patient, and may be custom-fit, such as by filing or other suitable method. With kit 800, the oral surgeon is able to select the proper tooth location from implants 500 in kit 800, and to then modify the configuration of the selected implant 500 to conform to the configuration of the cavity into which implant 500 is being inserted.

Figure 28:
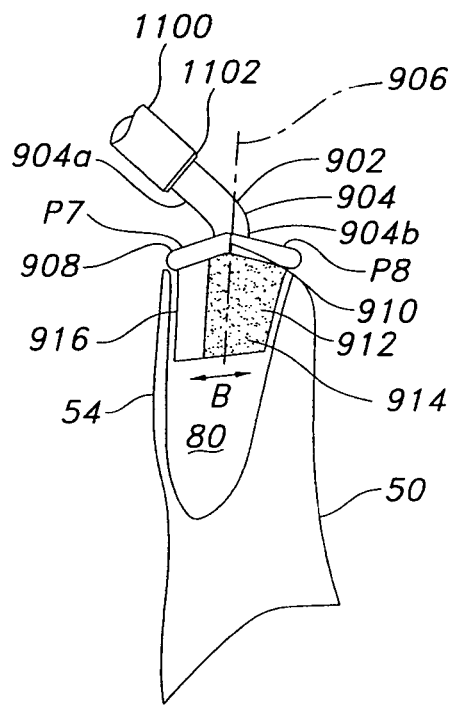
FIG. 28 is a mesial view of a fifth insertion tip being used to prepare a body cavity to receive the implant of FIGS. 19-23.
Figure 33:
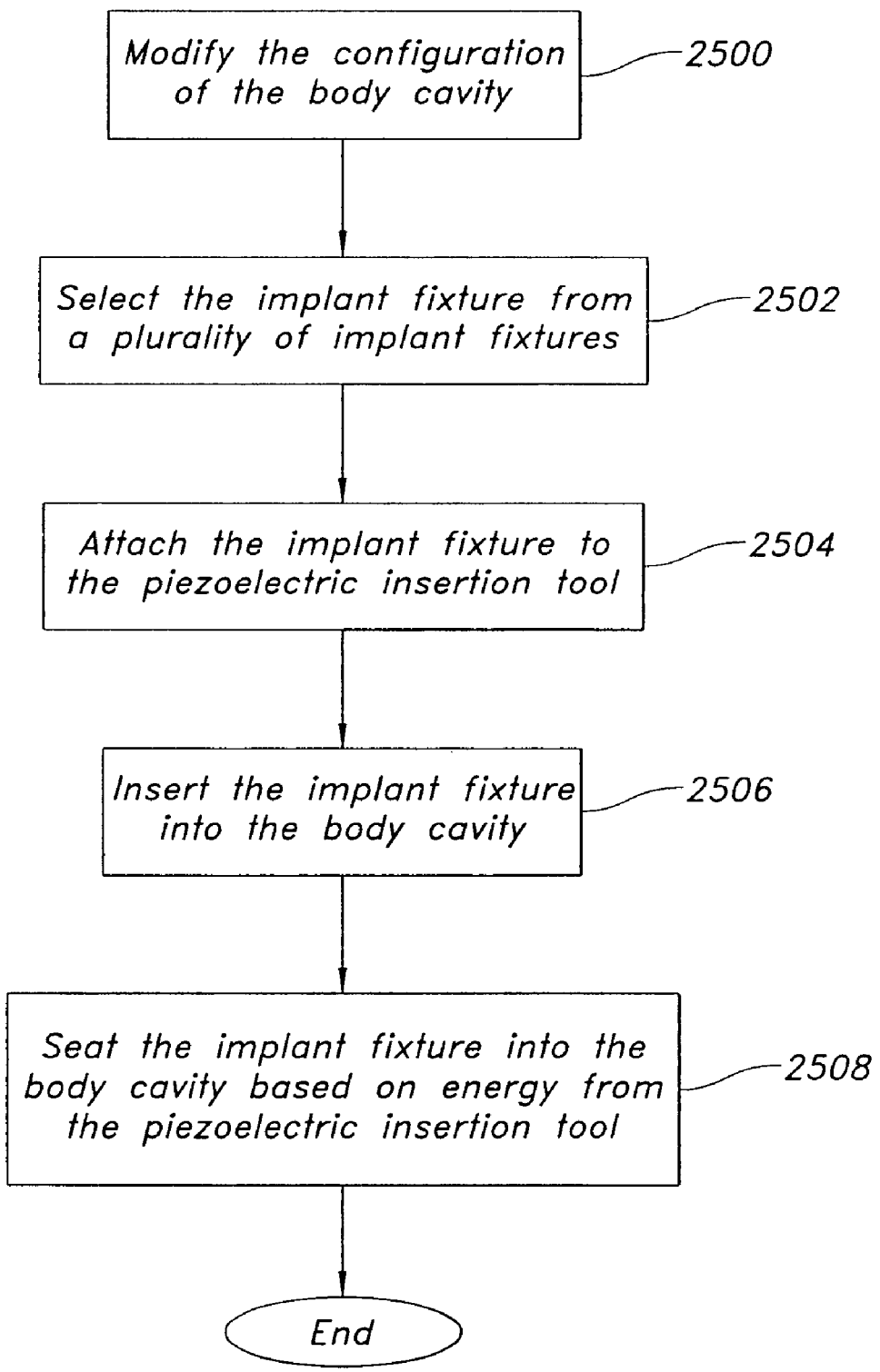
FIG. 33 is a flow chart illustrating the steps performed to insert the implant of FIGS. 19-23 into a patient.

One embodiment of a method of inserting implant 500 into a patient will now be described and is shown in FIGS. 28-32 and the flow chart of FIG. 33. FIG. 28 shows body cavity 80 with a damaged tooth having already been extracted therefrom. In step 2500, body cavity 80 is prepared by coupling a fifth insertion tip 902 to piezoelectric insertion tool 1100 and inserting fifth insertion tip 902 into body cavity 80. As shown in FIG. 28, fifth insertion tip 902 reflects the size and shape of body cavity 80 in the coronal one third. Fifth insertion tip 902 includes a shaft 904 that is releasably coupled to free end 1102 of piezoelectric tool 1100. Shaft 904 bends approximately ninety degrees with a first end 904a coupled to piezoelectric tool 1100 and a second end 904b extending along a longitudinal axis 906. Second end 904b of shaft 904 is connected to a generally circular flange 908. Flange 908 is formed along at least two planes, P7, P8 to mimic the compound angle of first end 510 of implant 500 (shown in FIG. 20). At least one of the planes P7, P8 extends obliquely relative to longitudinal axis 906. FIG. 28 shows planes P7 and P8 intersecting at bend 910.

As shown in each of FIGS. 28-31, the portion of bone 50 to the right side of tool 1100 is slightly higher than the portion of bone 50 to the right side of tool 1100. Bend 910 in flange 908 allows an operator to maintain an approximately even spacing between bone 50 and flange 908 as fifth insertion tip 902 is inserted into bone 50 as body cavity 80 is formed.

A cutting face 912 extends from flange 908, asymmetrically along longitudinal axis 906 and away from shaft 904. Cutting face 912 includes a rough cutting surface 914 that extends around only an aspect of cutting face 912. A facial aspect 916 of fifth insertion tip 902 has no active cutting surface in order to preserve the thin bone 54 on the facial side of bone 50. Operation of insertion tool 1100 vibrates fifth insertion tip 902 back and forth as shown by arrow B.

Figure 29:
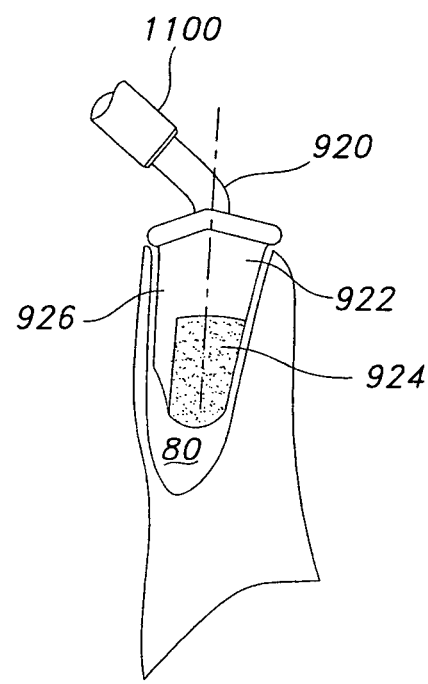
FIG. 29 is a mesial view of a sixth insertion tip being used to further prepare the body cavity of FIG. 28 to receive the implant of FIGS. 19-23.

After fifth insertion tip 902 has enlarged body cavity 80 to a desired size, fifth insertion tip 902 is then removed from body cavity 80 and piezoelectric tool 1100, and is replaced by a sixth insertion tip 920. As shown in FIG. 29, sixth insertion tip 920 is inserted in to body cavity 80 and reshapes the middle third of body cavity 80. Similarly to fifth insertion tip 902, sixth insertion tip 920 includes a rough cutting surface 924 that extends around only an aspect of a cutting face 922, but does not include an active cutting surface around a facial aspect 926 of sixth insertion tip 920.

Figure 30:
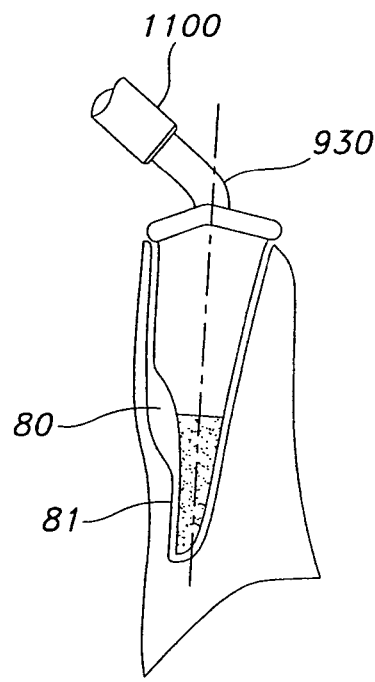
FIG. 30 is a mesial view of a seventh insertion tip being used to further prepare the body cavity of FIG. 29 to receive the implant of FIGS. 19-23.
Figure 31:
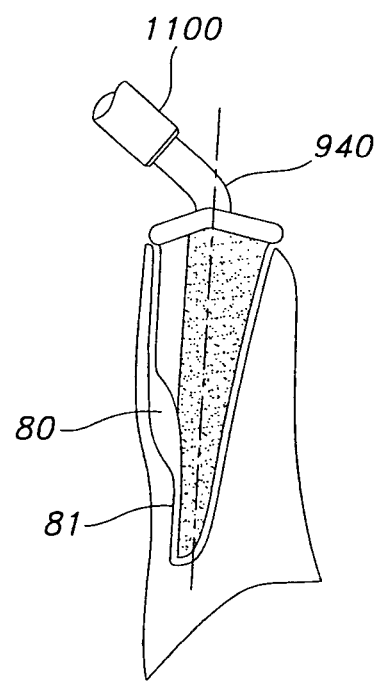
FIG. 31 is a mesial view of an eighth insertion tip being used to further prepare the body cavity of FIG. 30 to receive the implant of FIGS. 19-23.

Next, as shown in FIG. 30, sixth insertion tip 920 is replaced by a seventh insertion tip 930 that reshapes the apical third of body cavity 80 and forms a root extension 81. Root extension 81 increases the stability of implant 500 in body cavity 80. As shown in FIG. 31, an eighth insertion tip 940 is then used to refine opening defining body cavity 80.

As shown in FIG. 32, eighth insertion tip 940 is then removed from piezoelectric tool 1100 and an insertion tip 1110 is coupled to piezoelectric tool 1100. In step 2502, implant 500 is selected based on the tooth for which implant 500 and its associated crown 60 is being replaced. Implant 500 may be selected from kit 700 or 800 as described above. Alternatively, implant 500 may be selected from a plurality of implants 500, although not necessarily from a kit. Still alternatively, implant 500 may be from a stand-alone supply and need not necessarily be part of a kit.

In step 2504, implant 500 is coupled to insertion tip 1110. Insertion tip 1110 may include a nub 1112 that is inserted into opening 514 in implant 500 in a male/female relationship as shown by the arrow "C" in FIG. 32. Nub 1112 may provide at least a slight interference fit within opening 514 so that implant 500 remains coupled to insertion tip 1110 as implant 500 is inserted into body cavity 80 in step 2506, but yet still allow insertion tip 1110 to easily release from implant 500 after implant 500 is inserted into body cavity 80.

In step 2508, with implant 500 inserted into body cavity 80, as shown in FIG. 25, piezoelectric insertion tool 1100 embeds implant 500 into body cavity 80 based on vibrational energy generated by operation of piezoelectric insertion tool 1100. Implant 500 may be at least slightly larger than body cavity 80 so that implant 500 is force-fit into body cavity 80. Implant 500 engages walls 82 defining body cavity 80 in an interference fit.

Insertion of implant 500 into body cavity 80 is performed using ultrasonically generated vibrations without the need to rotate implant 500 about its longitudinal axis 530 within body cavity 80. Additionally, insertion of implant 500 within body cavity 80 may be performed without the use of an adhesive, although an adhesive, such as a biologically active cement that stimulates bone growth, may be used to further secure implant 500 into body cavity 80.

After implant 500 is securely inserted into body cavity 80, piezoelectric insertion tool 1100 is uncoupled from implant 500. Next, and illustrated in FIG. 25, crown 60 may be coupled to implant 500 as is described above with respect to implant 100. Alternatively, the crown may be cemented to implant 500.

While the above invention is described with respect to dental implants, those skilled in the art will recognize that the present invention may be adapted to other implants besides dental implants.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A device for forming a cavity in a bone, comprising:
    a shaft including a first end that is releasably couplable to a piezoelectric insertion tool and a second end extending along a longitudinal axis;
    a flange disposed on the second end of the shaft, wherein the flange defines a top face that is either connected to or extends from the second end of the shaft, a bottom face that is oriented opposite the top face and a side surface extending between the top face and the bottom face of the flange, wherein the top face extends along a plurality of planes that are non-parallel with respect to each other, and wherein at least one of the plurality of planes of the top face extends obliquely relative to the longitudinal axis of the shaft; and a cutting tool extending from the bottom face of the flange, the cutting tool including a cutting face that is configured to form a cavity in bone.

2. The device according to claim 1, wherein the cutting face extends around at least an aspect of the cutting tool.

3. The device according to claim 1, further comprising a non-cutting face extending around a facial aspect of the cutting tool.

4. The device according to claim 1, wherein the flange extends asymmetrically about the longitudinal axis.

5. The device according to claim 1, wherein the shaft is bent such that the second end of the shaft is aligned with the longitudinal axis and the first end of the shaft is not aligned with the longitudinal axis.

6. The device according to claim 1, wherein a perimeter dimension of the cutting tool is less than a perimeter dimension of the flange.

7. The device according to claim 1, wherein the plurality of planes form different angles with respect to the longitudinal axis of the shaft.

8. The device according to claim 1, wherein an elevation of the side surface of the flange with respect to the shaft is non-constant.

9. The device according to claim 1, wherein the plurality of planes of the flange intersect at a bend defined on the flange.

10. The device according to claim 1, wherein an entire surface of the cutting tool defines a cutting face.

11. The device according to claim 1, wherein the cutting surface extends across an entire perimeter of the cutting tool.

12. The device according to claim 1, wherein a circumference of the cutting tool is non-constant along a length dimension of the cutting tool.

13. The device according to claim 1, wherein the cutting face defines a substantially concave exterior surface.

* * * * *

UNITED STATES PATENT AND TRADEMARK OFFICE
CERTIFICATE OF CORRECTION

PATENT NO.        : 7,758,344 B2
APPLICATION NO. : 11/711815
DATED             : July 20, 2010
INVENTOR(S)       : Dumitru Gogarnoiu It is certified that error appears in the above-identified patent and that said Letters Patent is hereby corrected as shown below:

At Column 5, lines 32-43, "After implant 300 is inserted into bone 50, crown 80 is secured to implant 300. Crown 80 includes a recess 82 extending longitudinally therethrough. A bottom part of recess 82 narrows, forming a lip 89. A coupling, such as a screw 86, is inserted through recess 82 and extends beyond crown 80 and into opening 314 for a threaded connection with mating threads (not shown) in opening 314. Screw 86 engages lip 89 to retain the head of screw 86 within recess 82. Bottom surface 84 of crown 80 is contoured to mate with top face 312 of implant 300 to provide a close fit between crown 80 and implant 300. After crown 80 is screwed onto implant 300, a filler 90 is inserted into recess 82 to cover screw 86"

should read -- After implant 100 is inserted into bone 50, crown 60 is secured to implant 100. Crown 60 includes a passage 62 extending longitudinally therethrough. A bottom part of passage 62 narrows, forming a lip 64. A coupling, such as a screw 66, is inserted through passage 62 and extends beyond crown 60 and into opening 114 for a threaded connection with mating threads (not shown) in opening 114. Screw 66 engages lip 64 to retain the head of screw 66 within passage 62. A bottom surface 68 of crown 60 is contoured to mate with top face 112 of implant 100 to provide a close fit between crown 60 and implant 100. After crown 60 is screwed onto implant 100, a filler 70 is inserted into passage 62 to cover screw 66. --

At Column 6, line 5, "passage" should read -- recess --

At Column 6, line 6, "passage" should read -- recess --

At Column 6, line 8, "passage" should read -- recess --

At Column 6, line 11, "passage" should read -- recess --

At Column 6, line 15, "passage" should read -- recess --

Signed and Sealed this

Twenty-third Day of November, 2010

David J. Kappos
*Director of the United States Patent and Trademark Office*

At Column 7, line 63, "β32" should read -- β2 --

At Column 8, line 6, "β32" should read -- β2 --

At Column 8, line 8, "β31, β32" should read -- β1, β2 --

At Column 8, line 15, "β32" should read -- β2 --